United States Patent [19]

Heimburger et al.

[11] Patent Number: 4,562,072

[45] Date of Patent: Dec. 31, 1985

[54] PROCESS FOR THE PASTEURIZATION OF ANTIHEMOPHILIC CRYOPRECIPITATE (AHC) AND ANTIHEMOPHILIC CRYOPRECIPITATE PREPARED THEREBY

[75] Inventors: Norbert Heimburger, Marburg; Gerhardt Kumpe, Wetter; Wilfried Wormsbächer, Kirchhain; Hans M. Preis, Marburg, all of Fed. Rep. of Germany

[73] Assignee: Behringwerke Aktiengesellschaft, Marburg, Fed. Rep. of Germany

[21] Appl. No.: 540,172

[22] Filed: Oct. 7, 1983

[30] Foreign Application Priority Data

Oct. 9, 1982 [DE] Fed. Rep. of Germany ....... 3237512

[51] Int. Cl.[4] .............................................. A61K 35/16
[52] U.S. Cl. ..................................................... 424/101
[58] Field of Search ........................................ 424/101

[56] References Cited

U.S. PATENT DOCUMENTS 4,297,344 10/1981 Schwinn et al. ..................... 424/101
4,405,603 9/1983 Schwinn et al. ..................... 424/101

Primary Examiner—Sam Rosen
Attorney, Agent, or Firm—Finnegan, Henderson, Farabow, Garrett & Dunner

[57] ABSTRACT

A process for the pasteurization of antihemophilic cryoprecipitate (AHC) is described, wherein AHC is heated in the presence of calicum ions, an amino acid and a carbohydrate. The pasteurized AHC is used for the treatment of coagulation disturbances.

6 Claims, No Drawings

PROCESS FOR THE PASTEURIZATION OF ANTIHEMOPHILIC CRYOPRECIPITATE (AHC) AND ANTIHEMOPHILIC CRYOPRECIPITATE PREPARED THEREBY

The invention relates to a process for the pasteurization of antihemophilic cryoprecipitate (AHC), and an antihemophilic cryoprecipitate prepared thereby.

F VIII/vW concentrates from human plasma are used to treat patients with hemophilia A and those with von Willebrand's syndrome (vW syndrome). At the present day, the treatment is carried out not only for prophylaxis but also in part as self-therapy. The latter fact, together with the life-long treatment of the patients, demand that the products be well tolerated. Experience has shown that such products are those which are most highly purified, since a loading of proteins not only makes it more difficult to dissolve and use concentrates of this type but can also lead to sensitization toward foreign proteins, the side reactions associated with this, particularly when they occur during self-therapy, representing a great risk for the patient.

| Nomenclature relating to the factor VIII molecule |
| --- |
| F VIII assoc.Ag = F VIII AG = \| F VIII R:AG \| (related antigen) |
| F VIII v.Willebrand factor = F VIII vWF = \| F VIII R:CoF \| (ristocetin cofactor) |
| F VIII activity = F VIII C (coagulation) = \| F VIII C:AG \| (coagulation antigen)* |

*Since it is possible to inhibit the activity with homologous antibodies, reference is also made to a C antigen in this context. The names in boxed are used internationally.

F VIII concentrates of high purity and activity which are well tolerated are available for the treatment of hemophilia A. Moreover, a hepatitis-safe F VIII concentrate is disclosed in German Offenlegungsschrift No. 2,916,711.

However, surprisingly, F VIII concentrates do not exhibit an optimal therapeutic effect on the treatment of the vW syndrome although, according to in vitro tests, they contain F VIII R:AG and F VIII R:CoF in addition to F VIII:C. Apparently, the in vitro test which is used to detect the vW syndrome, the ristocetin cofactor test, does not correlate with the bleeding time.

On the other hand, antihemophilic cryoprecipitate has a good therapeutic effect on the vW syndrome. Thus the object of the invention was to prepare a pasteurized, and thus hepatitis-safe, AHC having good F VIII and vW activity.

The problem in achieving this object involved the presence of several sparingly soluble proteins in the AHC, such as, for example, fibrinogen and fibronectin, which, for example during heating to 60° C. for 10 hours, are denatured and precipitate out.

The object was achieved in principle as follows: an AHC solution is heated in the presence of Ca ions, an amino acid and a monosaccharide or oligosaccharide or sugar alcohol, the saccharide or the sugar alcohol being added before the amino acid.

The concentration of citrate should be less than 10 mmol/l, and addition of Ca ions is advantageous; otherwise gel formation occurs during pasteurization.

Thus the invention relates to a process for the pasteurization of antihemophilic cryoprecipitate (AHC), which comprises heating a solution of AHC in the presence of Ca ions, an amino acid and a monosaccharide or oligosaccharide or sugar alcohol.

Ca ions should be present at a concentration of at least 0.2 mmol/l and at most 100 mmol/l, preferably 5 mmol/l. They are preferably added in the form of a $CaCl_2$ solution.

At least one of the amino acids glycine, $\alpha$- or $\beta$-alanine, hydroxyproline, proline, glutamine, $\alpha$-,$\beta$- or $\gamma$-aminobutyric acid, preferably glycine, is preferably added. The concentration is 1–3 mol/l.

The carbohydrate which is preferably used is sucrose at a concentration of 35–60 g/100 ml of solution. Sucrose concentrations greater than 30 g/100 ml solution, preferably 60 g/100 ml, and glycine concentrations of about 2 mol/l are necessary for adequate stabilization during the pasteurization of AHC; when the concentrations are lower, coagula form during heating and the F VIII:C activity decreases (with less than 2 mol/l of glycine).

Moreover, the concentration of complexing agents as are used for removing the blood should be below 10 mM citrate and 5 mM EDTA. The observation that fibrinogen which is free of complexing agents does not coagulate and remains clear on heating leads to the conclusion that the denaturing is due to removal of Ca ions. Apparently, the fibrinogen binds the calcium so tightly that complexing agents in low concentrations are unable to remove it. In this context, it is significant that, using the same stabilizers, heating in the presence of 5 mmol of citrate produces a clear AHC solution while a coagulum forms with 5 mmol of EDTA.

It is not possible to state an exact concentration of Ca ions in this heterogeneous mixture, since, apart from factor VIII, fibrinogen, which is the major constituent in this fraction, is stabilized by $Ca^{2+}$. Most preferably, complexing agents should be absent but Ca ions should be present at a concentration of 0.2–100 mmol/l, preferably 5 mmol/l (Table 1).

The heating is continued until any infectious hepatitis B virus which is present in the AHC loses its infectivity. For this purpose, heating is carried out at a temperature between 30° and 80° C. for one minute to 48 hours, preferably at a temperature of 50° to 70° C. for 5–15 hours.

According to investigations with polyacrylamide gel electrophoresis, the AHC obtainable according to the invention is free of fibrinogen polymers; by reason of its high content of fibrinogen, F VIII:C, F VIII R:CoF and fibronectin, it is an optimal therapeutic agent for the treatment of hemophilia syndromes and the vW syndrome, particularly because it is regarded as hepatitis-safe as a result of the pasteurization. Another advantage is the good solubility of the product, compared with other cryo-solutions, and this is due to the removal of the sparingly soluble proteins and polymers, in particular fibrinogen.

The heated solution is diluted with a buffer solution, and accompanying and denaturing proteins are removed by a preliminary precipitation with glycine before the AHC is precipitated by increasing the glycine concentration to 2.2 mol/l, together with sodium chloride (12 g/100 ml). The residue from precipitation is isolated by centrifugation, dissolved, dialyzed, the factor VIII activity is determined and the concentration is adjusted to 6-8 U/ml; after filtration to clarify and sterilize, the solution is filled, in 100 ml portions, into 250 ml infusion bottles and freeze-dried.

The tests which are tabulated below were carried out:

TABLE 1
Stability to heat of AHC with various stabilizing additives

| Sucrose (g/100 ml) | Glycine (mol/l) | Citrate (mmol/l) | EDTA (mmol/l) | $Ca^{2+}$ (mmol/l) | After 10 h at 60° C. |
|---|---|---|---|---|---|
| 15 | 2 | 5 | — | — | precipitation* + coagulation |
| 30 | 2 | 5 | — | — | coagulation |
| 60 | 2 | 5 | — | — | clear |
| 60 | — | 5 | — | — | coagulation |
| 60 | 0.5 | 5 | — | — | almost clear |
| 60 | 1 | 5 | — | — | clear |
| 60 | 2** | 5 | — | — | clear |
| 60 | 2 | 5 | — | — | clear |
| 60 | 2 | 10 | — | — | coagulation |
| 60 | 2 | 20 | — | — | coagulation |
| 60 | 2 | — | 5 | — | coagulation |
| 60 | 2 | — | 10 | — | coagulation |
| 60 | 2 | — | — | 2.5 | clear |
| 60 | 2 | — | — | 5 | clear |
| 60 | 2 | — | — | 10 | clear |
| 60 | 2 | — | — | 25 | clear |

*The sucrose concentration is not sufficient to keep the fibrinogen in solution.
**This concentration of glycine is necessary to preserve the factor VIII:C activity during heating.

Table 2 contains the results of the tests of activity of AHC in 60 ml of untreated cryoprecipitate after heating at 60° C. for 10 hours.

In order to remove the products of denaturing which arise during heating, a 1.3 mol/l glycine precipitation can be carried out, and to remove the stabilizers and to concentrate the F VIII/vW protein, a 2.2 mol/l precipitation with glycine together with 12 g of NaCl/100 ml of solution can be carried out. The invention is illustrated in more detail by the example which follows.

I. Al(OH)$_3$ adsorption 250 g of cryo were dissolved, at 37° C., in sufficient 0.1 mol/l NaCl solution to produce 1 liter of solution, 80 ml of a suspension of 1 g of Al(OH)$_3$ in 100 ml of water were added and the mixture was stirred for 15 minutes. The Al(OH)$_3$ was then removed by centrifugation and discarded.

II. Stabilization and pasteurization

Sufficient aqueous CaCl$_2$ solution was added to 1,000 ml of cryo solution from I for the mixture to contain 5 mmol/l of Ca$^{++}$, and 1,000 g of sucrose was added at 37° C. As soon as the sucrose had dissolved, 150 g of glycine were added and this was dissolved. The pH was adjusted to 7.3 with 2N NaOH, and the solution was then heated at 60° C. in a water bath for 10 hours.

Isolation of the proteins

III. Removal of accompanying proteins and products of denaturing

The solution obtained in II was cooled, diluted with 5 liters of citrate/NaCl buffer (0.06 mol/l of NaCl and 0.02 mol/l of tri-Na citrate), 648 g of glycine were added at 37° C. with stirring and, after 15 minutes, the mixture was cooled to 15° C. and centrifuged. The residue was discarded.

IV. Isolation of the F VIII/vW complex 449 g of glycine were added to the supernatant from III at 37° C., with stirring, and then 798 g of NaCl were stirred in so that the NaCl concentration was 12 g/100 ml. After all the additives had dissolved, the solution was cooled to 15° C. A clear separation of the precipitate from the supernatant was achieved by centrifugation at 3,000×g. The residue was dissolved in 200 ml of buffer (0.06 mol/l of NaCl, 0.02 mole/l of tri-Na citrate, pH 7.3, and 1 g of glycine/100 ml). 350 ml of solution were obtained.

V. Dialysis

The solution was dialyzed against 20 liters of the

TABLE

| Additives | | | | F VIII:C Activity | | | Activities after heating* | | |
|---|---|---|---|---|---|---|---|---|---|
| sucrose (g/100 ml) | glycine (mol/l) | citrate (mmol/l) | Ca$^{++}$ (mmol/l) | remaining after heating (%) | Volume (ml) | OD$_{280}$ | F VIII:C | F VIII R:AG | F VIII/vW |
| 60 | 2 | — | — | 96 | 38 | 14.1 | 5.6 | 20 | 10 |
| 60 | 2 | — | — | 95 | 40 | 13.0 | 8.8 | 24 | 14 |
| 60 | 2 | — | 2.5 | 90 | 42 | 14.5 | 4.8 | 17 | 8.6 |
| 60 | 2 | — | 5 | 86 | 45 | 16 | 8.0 | 32 | 14 |
| 60 | 2 | — | 10 | 88 | 64 | 10 | 5.6 | 17 | 9.8 |
| 60 | 2 | 5 | — | 96 | 40 | 12.9 | 4.8 | 20 | 10 |

*In units per ml relative to the activity of 1 ml of citrated plasma (= 1U)
Test procedure for
F VIII:C: Single-phase method of Simone et al. ; J. Lab. Clin. Med. 69,706 (1967)
F VIIIR:AG Electroimmunodiffusion method of Laurell; Analyt. Biochem. 15,45 (1966)
F VIII:vW: Platelet agglutination test using von Willebrand factor reagent from Behringwerke, Rivard et al.; Thromb. Res. 12,677 (1978)

EXAMPLE

Preparation of pasteurized AHC

Starting material: 250 g of untreated cryoprecipitate (cryo) as is produced after separation from citrated plasma (G. Pool: Cryoprecipitate: its Preparation and Clinical Use; Handbook of Hemophilia; ed. K. M. Brinkhous and H. C. Hemker, Part II, 1975).

same buffer as in IV, this leading to 400 ml of solution with a conductivity of 14 mS.

VI. Final formulation

For this purpose, ultracentrifugation, filtration to clarify and filtration to sterilize were subsequently carried out. Yield: 500 ml of pasteurized AHC solution were obtained and, where appropriate, this was freeze-dried.

Three batches of pasteurized AHC prepared by the process described in the example were characterized as follows:

Activities after dissolving 1,720 mg of lyophilizate in 50 ml of distilled water

| Batch | F VIII:C R:AG R:CoF (units per ml, relative to activity in 1 ml of citrated plasma) | F VIII R:AG | F VIII R:CoF | Fibrinogen (mg/100 ml) | Fibronectin (mg/100 ml) | Fibrinogen, method of Blomback Percentage of coagulable protein |
|---|---|---|---|---|---|---|
| 1 | 7 | 31 | 12 | 863 | 193 | 79 |
| 2 | 6.8 | 27 | 20 | 1189 | 218 | 79 |
| 3 | 8.8 | 29 | 15 | 1243 | 246 | 79 |

The activity of F VIII:C in all three batches is of the order of about 35% of the theoretical figure relative to the starting material used as cryo; the corresponding figure for F VIII R:CoF is 100%.

We claim:

1. A process for the pasteurization of antihemophilic cryoprecipitate (AHC), which comprises heating a solution of AHC in the presence of effective amounts of Ca ions, an amino acid and a monosaccharide or oligosaccharide or sugar alcohol for a time sufficient to inactivate hepatitis virus in said solution of AHC wherein said Ca ions are present in a concentration of about 0.2 mmol. to about 100 mmol. per liter and wherein said Ca ions, amino acid, and monosaccharide or oligosaccharide or sugar alcohol are present in effective amounts such that the pasteurized antihemophilic cryoprecipitate (AHC) is substantially free of fibrinogen polymers.

2. The process as claimed in claim 1, wherein the amino acid is selected from the group consisting of glycine, α- or β-alanine, hydroxyproline, proline, glutamine and α-, β- or γ-aminobutyric acid and said amino acid is present in a concentration of 1–3 mol/l.

3. The process as claimed in claim 1, where the oligosaccharide is surcrose and said surose is present in a concentration of 35–60 g/100 ml of solution.

4. The process as claimed in one of claims 1 and 2–3, wherein the solution of AHC is heated at a temperature of 50°–70° C. for 5–15 hours.

5. Antihemophilic cryoprecipitate prepared by the method of one of claims 1 and 2–4 and containing soluble fibrinogen and fibronectin; and being substantially free of fibrinogen polymers.

6. The process of claim 1 wherein said solution of AHC is treated with Al(OH)$_3$ prior to said heating of said AHC solution.

* * * * *